United States Patent
Seckel

(10) Patent No.: US 8,286,639 B2
(45) Date of Patent: Oct. 16, 2012

(54) METHOD FOR NON-SURGICAL FACIAL REJUVENATION

(76) Inventor: Brooke R. Seckel, Concord, MA (US)

( * ) Notice: Subject to any disclaimer, the term of this patent is extended or adjusted under 35 U.S.C. 154(b) by 995 days.

(21) Appl. No.: 11/546,788

(22) Filed: Oct. 12, 2006

(65) Prior Publication Data

US 2007/0079838 A1    Apr. 12, 2007

Related U.S. Application Data

(60) Provisional application No. 60/725,858, filed on Oct. 12, 2005.

(51) Int. Cl.
*A61B 19/00* (2006.01)
(52) U.S. Cl. ............ 128/898; 424/401; 601/17
(58) Field of Classification Search .......... 601/17; 424/401
See application file for complete search history.

(56) References Cited

U.S. PATENT DOCUMENTS

| | | | |
|---|---|---|---|
| 2003/0152610 A1* | 8/2003 | Rolf et al. | 424/449 |
| 2005/0148906 A1* | 7/2005 | Skover et al. | 601/17 |
| 2005/0148910 A1* | 7/2005 | Skover et al. | 601/46 |
| 2006/0003033 A1* | 1/2006 | McClellan et al. | 424/729 |
| 2006/0237021 A1* | 10/2006 | Guay et al. | 128/898 |
| 2007/0065396 A1* | 3/2007 | Morariu | 424/74 |

OTHER PUBLICATIONS

Comprehensive treatment of the aging face—cutaneous and structural rejuvenation by Sherris DA, Otley CC, Bartley GB. Mayo Clin Proc. Feb. 1998;73(2):139-46.*
Multimodality aesthetic skin rejuvenation by Gentile RD Facial Plast Surg. May 2005;21(2):120-30.*

* cited by examiner

*Primary Examiner* — Henry M Johnson, III
*Assistant Examiner* — Jeffrey B Lipitz
(74) *Attorney, Agent, or Firm* — Kristofer E. Elbing

(57) ABSTRACT

A method for non-surgical rejuvenation of facial skin to correct both Type 1 aging changes in the epidermis layer of the skin causing visual changes in the skin and Type 2 aging changes in the dermis layer of the skin causing damage to supportive elements of the skin. The method includes the steps of exfoliation of the facial skin, stimulation of new dermal collagen deposition, removal of at least one of pigment and superficial blood vessels, relaxation of facial expression muscles, filling of soft tissue defects including at least one of deep facial lines and contour deformities, and tightening of the facial skin, and the steps of the method are applied according to a selected one of a plurality of age determined regimens.

8 Claims, 2 Drawing Sheets

METHOD FOR NON-SURGICAL FACIAL REJUVENATION

CROSS REFERENCES TO RELATED APPLICATIONS

The present Application is related to and claims benefit of co-pending U.S. Provisional Patent Application Ser. No. 60/725,858 filed Oct. 12, 2005 by Brooke R. Seckel for a METHOD FOR NON-SURGICAL FACIAL REJUVENATION.

FIELD OF THE INVENTION

The present invention relates to rejuvenation of facial superficial and dermal layer rejuvenation of facial skin to reverse, alleviate or delay normal aging processing and, in particular, to a non-surgical method for rejuvenation of facial skin.

BACKGROUND OF THE INVENTION

Increasing life expectancy has created large dynamic, active and vocal population subset in the United States consisting of people over the age of 40. Coupled with the major movement of women into the workplace and highly marketed youth oriented lifestyle ideals, there is an increasing national preoccupation with the field of anti-aging in general, and maintaining a fit and youthful facial appearance in particular.

The magnitude of this phenomenon can be inferred from the fact that Americans spend over $28 Billion a year on anti-aging face creams (most of which are ineffective), and last year 12.4 million Plastic Surgery operations were performed, over half of which were done to "rejuvenate the face.

In spite of this major effort and expenditure, few if any facial rejuvenation procedures effectively reverse the signs of facial aging and restore an aging face to a truly youthful appearance. The reasons are many and reflect a "one size fits all" approach to the field of facial aging and it's rejuvenation by the cosmetic, pharmaceutical, medical, and plastic surgery industries. Additionally, the fact that the most effective current facial rejuvenation methods require surgery dissuades many from pursuing facial rejuvenation for fear of having surgery. The immense demand for non-surgical facial rejuvenation and the lack of effective non-surgical facial rejuvenation techniques have led to a plethora of heavily marketed ineffective one size fits all facial rejuvenation schemes from wrinkle creams to, in one case, an incredible $10,000.00 week end "face lift in Manahatten which consists primarily of eating salmon and taking vitamins.

A major problem of the rejuvenation methods of the prior art is that most if not all current facial rejuvenation methods are uni-modal and as such fail to address the fact that facial aging changes are multifaceted and a combination of many physiological, histological, and structural changes that occur over a lifetime. The attempt to correct facial aging with one modality which can correct only one or a few components of the facial aging process will only achieve a partial correction or no correction at all.

To better understand the requirements for a truly effective facial rejuvenation technique one must understand the basic components of the facial aging changes that produce an aged appearance to the face, which may be illustrated by a visual comparison of a young face, such as that of an infant or child, and an old face, such as that of a person in their forties or older.

While it is apparent that the appearance of the child's facial skin is strikingly different from that of an older adult, it is helpful to objectively define the significant age related changes of the adult man's skin that are in fact due to aging as opposed to those changes that are related to the growth and development of the person, that is, the maturation process by which a person develops from childhood to adulthood. A realization and understanding of the "aging processes" and effects separate and apart from the maturation processes will assist in understanding what structural elements or aspects of a persons face have to be altered, or "rejuvenated", and in what manner, to restore a youthful appearance to an older person's face.

Many of the age related facial changes that need to be modified for effective facial rejuvenation are illustrated in FIG. 1 shows an illustrative aged face 10A on the left side of the image and, for comparison, a illustrative youthful face 10B on the right side of the image. As illustrated therein, the facial changes and effects resulting from aging, as opposed to maturation, may include, for example, frown lines 12A, "bunny" lines 12B, "worry" lines 12C, brow ptosis 12D, eyelid laxity 12E, "crow's feet" 12F, eyelid bags 12G, tear through deformities 12H, nasal labial folds 12I, "marionette" lines 12J, platysmal bands 12K and "lipstick" lines 12L.

Facial skin aging changes such as those illustrated in FIG. 1 may be generally categorized into Type 1 and Type 2 facial aging changes. Type 1 aging changes are superficial and may be observed as changes in the superficial layer of the skin called the Epidermis. Type 1 aging changes may be illustrated by comparison of a child's face with an older adult's face wherein it will be apparent that the child's skin appears smooth, moist, free of blemishes, spots and wrinkles. By contrast, the older adults skin appears rough, dry, and sallow, with multiple brown spots, red spots, and wrinkles. The causes of these visible superficial changes are multi-factorial and include heredity, exposure to UV light from the sun and toxins, and molecular aging events involving DNA in the body's cells. The surface cells of the skin are histologically abnormal, which gives a dry dull cast to the skin, and multiple brown pigment and red blood vessel spots create a non-uniform blemished appearance to the skin and wrinkles are a pathognomonic sign of facial aging that everyone recognizes.

Type 2 facial aging changes are the result of changes in the deeper portion of the skin called the Dermis wherein aging results in severe damage to the dermis primarily as destruction and loss of collagen and elastin, which are major supportive elements of the dermis that provide elasticity, firmness, and fullness to the facial skin. Aging also results in atrophy of the subcutaneous (beneath the skin) fat, which results in looseness of the skin and thinning of the skin. The effect of these changes is seen in the aged face 10A of FIG. 1 where the aged skin can be seen sagging and falling into folds over the face.

Another type2 facial aging change is caused by the action of the muscles of facial expression that pull on the skin as they express our emotions. Over a lifetime the repeated action of these muscles produces the lines of facial expression, frown lines, crow's feet, worry lines and bunny lines, all of which, when they become permanent, provide a classic, easily recognizable appearance of facial age.

The final component of facial aging that contributes to an aged facial appearance is slow, gradual bone atrophy, which contributes minimally but further to the facial sagging and downward descent of the facial skin as the underlying structural support of the bone is gradually lessened.

Therefore considering the current state of the art of facial rejuvenation therapies, the "gold standard" of facial rejuvenation therapy has for many years been the plastic surgical procedures known as the face-lift, or rhytidectomy, and the eyelid rejuvenation procedure known as the blepharoplasty. As is well known in the relevant arts, these surgical procedures remove a portion of the damaged aged skin through incisions around the ear and on the eyelids and, when the incisions are closed, the remaining aged skin is pulled tighter as the result of the loose skin being removed. While the facial and eyelid contours are improved, the remaining skin on the face is still aged and displays both Type 1 and Type 2 facial aging changes, so that while the patients are left with a tighter face, the facial skin is still aged in appearance, which is hardly an effective facial rejuvenation. Fears of surgery and the possibility of serious complications such as facial paralysis have also limited the acceptance and thus application of these surgical techniques.

Another rejuvenation method of the prior art is facial resurfacing operations, such as chemical peel and laser resurfacing procedures, have also been used and which do effectively remove wrinkles and provide some skin tightening. Effective facial rejuvenation, however, requires a deep "peel" which results in loss of skin pigment which in turn creates an unsightly demarcation line below the jaw where old skin stands out on the neck when compared to the resurfaced skin on the face. Complications such as scarring are also very common. Because of these complications, such procedures have not gained wide acceptance by physicians and patients.

In the early 1980's yet another rejuvenation method that involved injectable collagen was introduced wherein the collagen serves as a soft tissue filler that is injected into the face beneath wrinkles, scars, and deep facial lines to plump or fill out these aging associated facial depressions. While initial results were encouraging, the soft fillers "plumped up" lines and wrinkles, but did not correct Type 1 surface changes and did not address the facial laxity associated with aging. The use of injected collagen or other soft tissue fillers was further limited by the fact that the effect of such injections lasted only 6 weeks to 3 months because of degradation of the filler within the body, and by the fact that many people were allergic to the soft tissue fillers.

In the past three years improved soft tissue fillers have been introduced using, for example, hyaluronic acid, polymethyl methacrylate, calcium hydroxy apatite, polyglycolic acid, bioengineered human skin type 1 collagen, cultured fibroblasts, morselized cadaver tendon and collagen, and autogenous fat and dermis. All of these agents have beneficial initial effects but all are temporary as their effect lasts at most a year. More importantly, however, is the fact that soft tissue filler injections are uni-modal and address only one aspect of facial skin aging, that is, the loss of volume secondary to atrophy of subcutaneous fat and dermis.

In the mid 1990's a new high tech revolution in the field of facial rejuvenation began with the introduction of the laser as a new facial rejuvenation tool. In 1995 the CO2 laser was introduced as a facial resurfacing tool, followed several years later by the Erbium laser, which was a significant improvement over the CO2 laser because the Erbium laser produced less heat and thus less injury to the facial skin and thus fewer complications. Radiofrequency energy was also used for this purpose.

These technologies have not gained wide acceptance, however, because they are ablative procedures, which means that the skin is ablated or surgically removed, necessitating a prolonged period of surgical recovery or "down time", with have associated complications, such as hypopigmentation (loss of skin color), scarring, and demarcation lines. In addition, they remain uni-modal and do not address all of the Type 2 facial aging changes, such as the lines of facial expression and subcutaneous fat atrophy.

Since 2000 a new class of non-ablative technologies have been introduced to rejuvinate the facial skin without the limitations imposed by the surgical recovery times and complications of the ablative laser procedures. These new non-ablative procedures utilize laser, intense pulsed light, radiofrequency, and infrared energies to injure the deep layers of the skin, that is, the dermis, to stimulate a healing response, that is, a controlled scar, which results in the formation of new collagen to replace the damaged aged collagen previously present in the skin. The theory is that if new collagen can be produced to replace the aged damaged collagen, skin texture and elasticity will be restored, the skin will be plumped and wrinkles will be removed. As a practical matter, the best results achieved by the most successful technologies show at best a 20% reduction of fine facial wrinkles only after 5-7 treatments over a period of 7 months. Again these technologies are uni-modal in that they leave type1 superficial changes unaltered and thus at best achieve only a partial facial rejuvenation effect, and have associated undesired side effects such as discussed above.

A group of related procedures have been used concurrently with the above discussed "non-ablative" methods to remove Type1 facial aging changes, such pigment (brown spots) and vessels (red spots) through a process called selective photothermolysis, that is, light destruction of cells by selective heating. These technologies have been remarkably successful in correcting pigmentary (brown spot) and vascular (blood vessel) Type 1 facial aging changes, but do not address neither the textural type 1 changes nor the Type 2 deeper facial aging changes. A new (2005) laser modality, referred to as the Fraxel® laser, does address pigment and texture problems and possibly promotes new collagen production, but does not remove vessels and does not tighten the skin, so that this method again addresses only a portion of the effects that must be addressed to achieve satisfactory skin rejuvenation. skin Again, all of these technologies deliver significant thermal energy to the skin and must be accompanied by sophisticated cooling devices to avoid burn injury to the skin, and the risk of skin injury by inappropriate or incorrect use remains a significant risk to the patient in terms of scarring.

In the past three years (2002-2005), radiofrequency and infrared energy have been utilized to deliver heating to the deeper dermis layer of the skin in an attempt to modify or remodel the collagen in the dermis to a shorter more compact configuration in an attempt to tighten the skin. The best clinical studies to date have demonstrated at best a 30% tightening of the skin in 30% of patients treated, most commonly only patients with thinner skin and little subcutaneous fat. Furthermore, the risk of thermal injury to the skin is present, requiring sophisticated skin cooling devices during treatment. Effective results also require expert application of the technique, a time consuming fastidious process, and repeated (3-5) treatments over a period of 5-7 months. In the most successful cases, however, the Type 1 facial aging changes are not addressed, leaving tightened but old looking skin on the surface, again a result of a uni-modal approach to a multifaceted problem.

It will be noted that none of the above discussed therapies address Type 2 facial aging changes caused, for example, by the contraction of the muscles of facial expression, the crow's feet, worry lines, frown lines, and bunny lines, which are the general hallmarks of an aged facial appearance. In the past two years, the use of a muscle-paralyzing agent, such as Botox®, has been effectively used to relax the muscles of facial expression and remove the lines associated with musclecontraction. Botox®, which was FDA approved in 2004, has gained wide popularity as a useful agent in facial rejuvenation for reducing or eliminating the lines of facial expression. Its usefulness is limited, however, by the fact that its effect is temporary, lasting only 6 months to one year. In addition, and like the other methods discussed above, Botox® is uni-modal therapy having no effect on Type 1 facial aging changes and only addressing one of several Type 2 facial aging changes.

The net result after nearly a half -century of research and development and the expenditure of many millions of dollars is that the goal of rejuvenating an aged facial appearance remains an elusive yet much sought after goal. While an aging face does not threaten the life of the individual, the contribution to quality of life for a significant and likely increasing highly motivated segment of the population is significant, as demonstrated by the enormous financial expenditures both by patients and commercial research endeavors in this field.

The present invention provides a solution to these and related problems of the prior art.

SUMMARY OF THE INVENTION

The present invention is directed to a method for non-surgical rejuvenation of facial skin wherein the method includes the steps of exfoliation of the facial skin, stimulation of new dermal collagen deposition, removal of at least one of pigment and superficial blood vessels, relaxation of facial expression muscles, filling of soft tissue defects including at least one of deep facial lines and contour deformities, and tightening of the facial skin.

The method may further include the steps of correcting of at least one of atrophy of subcutaneous fat and loss of bone, and at least one of a dietary regime, an exercise regime and an administering of vitamin supplements.

The step of exfoliation of the facial skin may include application of an emollient, mechanical exfoliation, and laser peeling and the step of removal of at least one of pigment and superficial blood vessels may include application of a pigment and vessel control agent, mechanical exfoliation, dermal abrasion, laser peeling, and light therapy.

The step of filling of soft tissue defects may include application of a skin plumping agent and injection of a soft tissue filler and the step of tightening of the facial skin may include radiative energy therapy and abrasive resurfacing of the skin.

The step of stimulation of new dermal collagen deposition may include application of an anti-oxident agent, application of collagen stimulating agent, and laser light therapy, and the step of relaxation of facial expression muscles may include injection of a muscle paralyzing agent or a muscle relation agent.

The method is performed as at least one of a plurality of age dependent rejuvenation regimens wherein each regimen includes steps selected from the steps of the method and include a preventative regimen, an early facial aging regimen, a moderate facial aging regimen, and a mature facial aging regimen, and wherein each regimen incorporates agents and procedures corresponding to Type 1 and Type 2 aging effects to be corrected. According to the present invention, the aging effects corrected by the method of the present invention include Type 1 aging changes in the epidermis layer of the skin causing visual changes in the skin and Type 2 aging changes in the dermis layer of the skin causing damage to supportive elements of the skin.

BRIEF DESCRIPTION OF THE DRAWINGS

The invention will now be described, by way of example, with reference to the accompanying drawings in which.

DESCRIPTION OF THE PREFERRED EMBODIMENTS

As demonstrated in the above discussions of the prior art, effective facial rejuvenation or the restoration of a youthful facial appearance requires a multi-modal approach since the factors which produce an aged facial appearance are multi-factorial and cannot be altered or reversed by the correction of one aging change alone.

The present invention is thereby directed to a multi-modal, synchronized, step by step therapeutic program which addresses all Type 1 and Type 2 facial aging changes in an appropriately sequenced manner to accomplish effective facial rejuvenation.

According to the present invention as described below, the multimodal corrective measures of the present invention must be applied in the appropriate sequence to effect satisfactory facial rejuvenation without complications, unsatisfactory consequences, or failure to achieve successful facial rejuvenation.

It must be noted in the following descriptions of the method of the present invention that at least certain of the method steps include the application of various agents, creams or other liquid/gel treatments. The following descriptions indicate the types of such agents that may be employed in the method steps of the present invention, and also identifies certain specific commercially available products that may be used for the described purposes. Further descriptions of these agents, and of the method steps and such factors as diet and exercise regimes may be found, for example, in Appendix A hereto, which is a publication titled "Save Your Face" by Brooke Rutledge Seckel, M.D., published in 2005 by Peach Publications of Concord, Mass., the contents of which are incorporated herein by reference.

Figure 1:
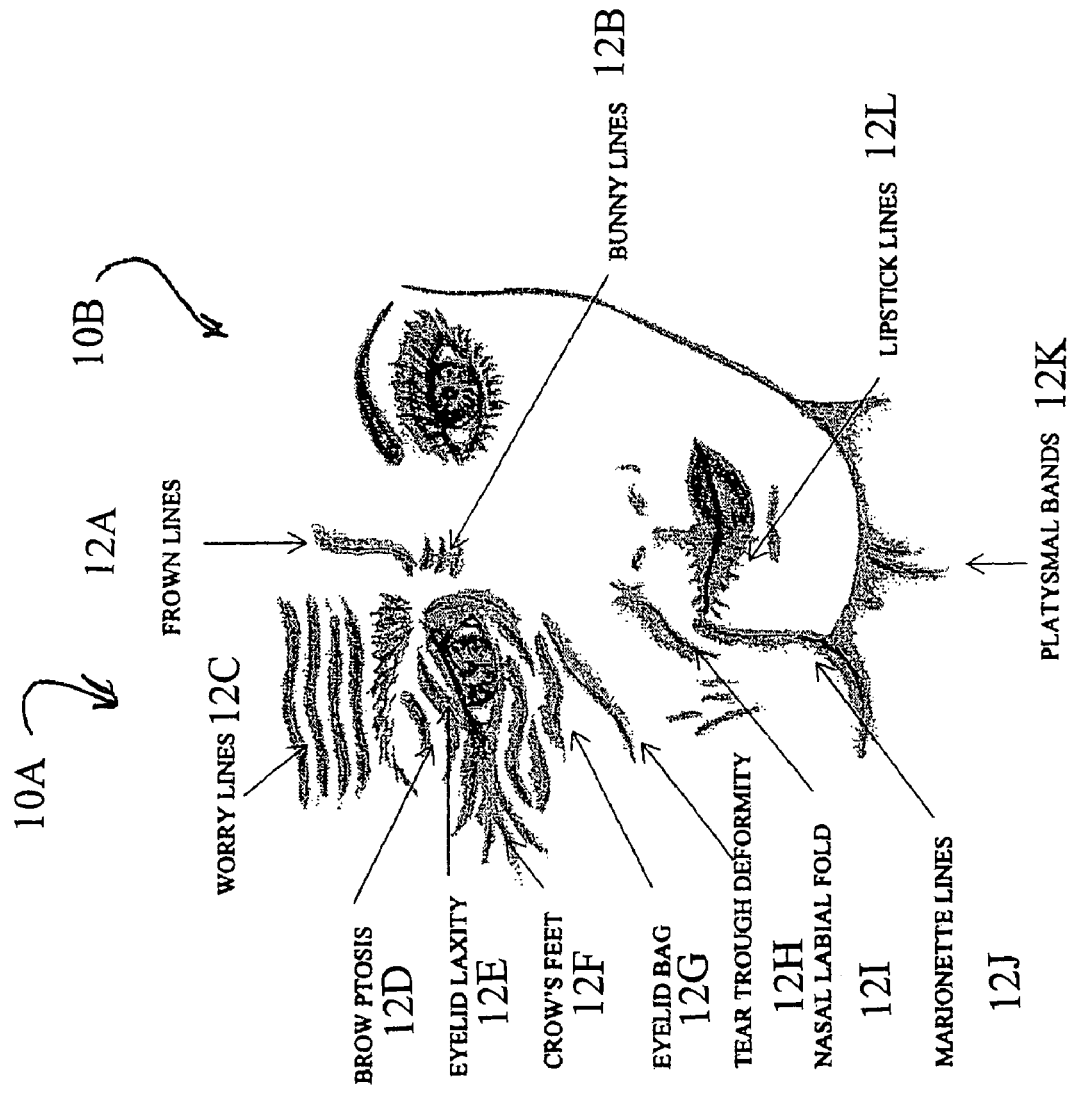
FIG. 1 is a diagrammatic illustration of aging effects in facial skin.
Figure 2:
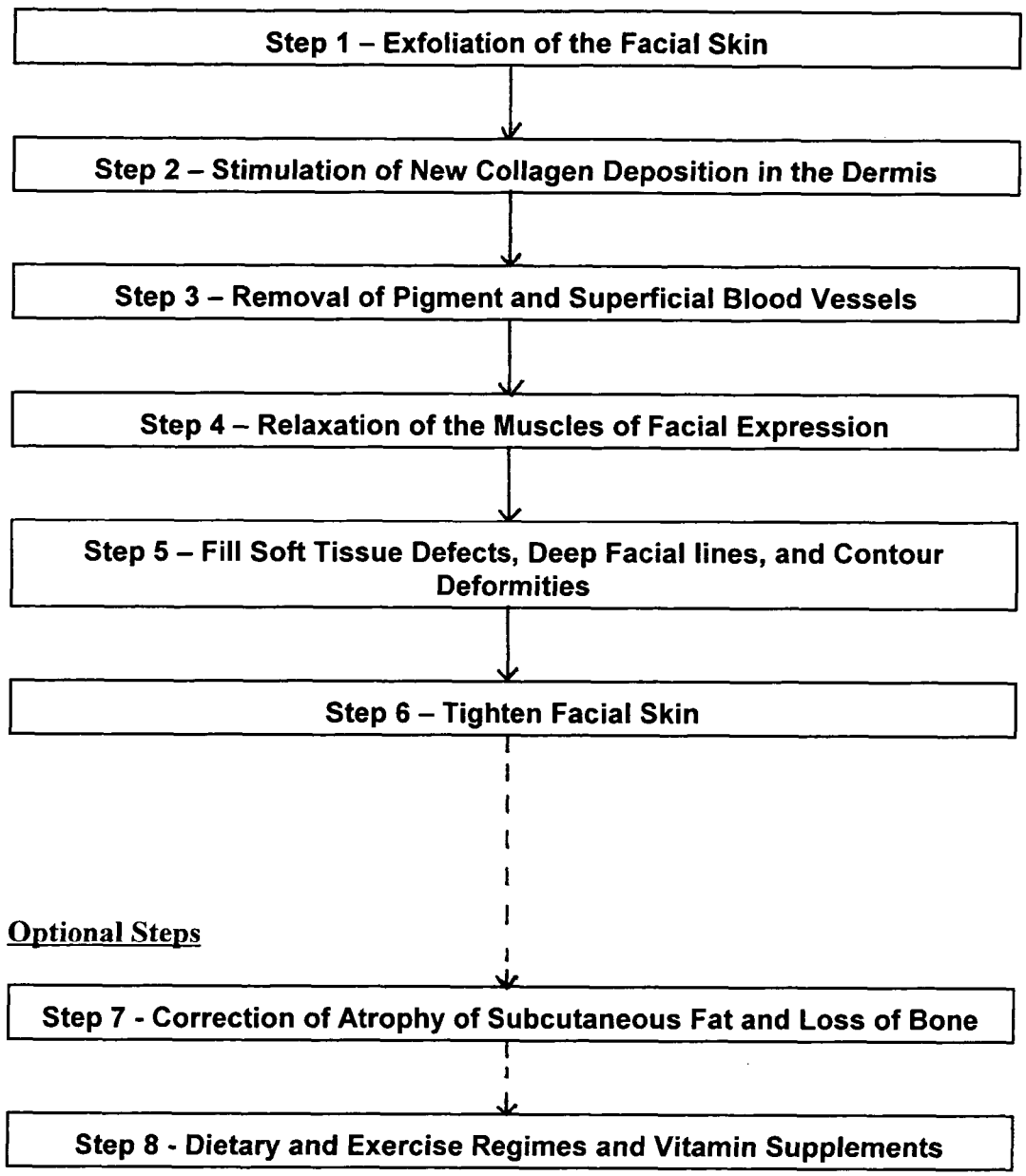
FIG. 2 is a flow diagram illustrating the steps of the facial skin rejuvenation method of the present invention.

In brief, the facial skin rejuvenation method of the present invention as illustrated in FIG. 2 includes the steps, in the presently preferred order in which they are performed, of:

1. The removal, that is, exfoliation, of aged surface skin cells to restore a youthful texture to the skin—a step to correct Type 1 facial aging changes;

2. Stimulation of new collagen deposition to plump the skin and lessen the appearance of wrinkles and improve skin texture—a step to correct Type 1 and Type 2 facial aging changes;

3. The removal of pigment and abnormal visible blood vessels from the skin surface—a step to correct Type 1 facial aging changes;

4. Relaxation of the muscles of facial expression to eliminate the lines of facial expression, crow's feet, worry lines, frown lines, and bunny lines—a step to correct Type 2 facial aging changes;

5. Filling or plumping the facial skin, especially in areas affected by deep facial lines and contour deformities—a step to correct Type 2 facial aging changes; and, 6. Tightening facial skin—a step to correct Type 2 facial aging changes.

The method of the present invention may also include a step 7, which is the correction of laxity and contour deformities created by facial volume loss secondary to atrophy of the subcutaneous fat and loss of bone associated with aging. This is a step to correct Type 2 facial aging changes and is performed as necessasry.

The method of the present invention will also typically include specific dietary and vitamin supplements with agents that are administered to prevent and reverse facial and skin aging, and which may be regarded as an eighth step.

It must be noted that the steps of the method of the present invention are listed above in the presently preferred order in which they are performed, and that the sequence of steps is selected so that, for example, one step is preparatory for a following step or so that the results of a step will not be negated or eliminated by a following step. It should also be noted, however, that some variation in the sequence of steps is possible depending, for example, on the circumstances of a particular patient, the particular procedure to be used in a given step, such as laser peeling as opposed to chemical or mechanical abrasion, and so on, and the preferences of the person performing the method on the patient. For example, steps 2 and 3 of the method as listed above may be reversed, depending upon circumstances, and such variations are considered to be within the scope of the present invention.

Therefore considering each of the above described steps of the method of the present invention in greater detail:

Step 1—Exfoliation of the Facial Skin

Exfoliation involves the mechanical or chemical removal of dead skin cells from the surface of the face. Exfoliation contributes several beneficial rejuvenating effects to the skin surface, such as:

Removal of dead skin cells—the outer surface of the skin has many layers of dead skin cells which pushed upward to the skin surface by the actively growing new skin cells produced by the basal cell layer of the epidermis which is the deepest layer of the epidermis. These new cells are plumper, have more moisture and after the dead cells are removed by exfoliation they are exposed revealing a healthy glowing more youthful appearing cast to the skin surface Better penetration of rejuvenating topical agents—The dead skin cells form a barrier to the penetration of topically applied agents intended to remove pigmentation and stimulate new skin cell formation in the epidermis and collagen production in the dermis.

Removal of skin pore blocking debris—dead skin cells and dirt and environmental debris and skin oils accumulate on the surface of the skin and block the pores of the skin. This blockage can lead to accumulation of skin oils and sweat which can cause milia—small cysts—and acne and result in an uneven texture to the skin.

Mild irritation of the dermis—stronger exfoliants such as glycolic acid, Retin A, and microdermabrasion® can produce mild dermal irritation and actually result in the formation of new collagen deposition in the superficial dermis. Removal of superficial epidermal pigmentation—superficial pigmentation, brown spots are a classic Type 1 facial aging change. Much of this pigmentation, which is present in the epidermis, may be removed with vigorous exfoliation, and topical agents intended to remove pigment in the deeper layers can more easily penetrate the skin to exert their effect after exfoliation.

Step 2—Stimulation of New Collagen Deposition in the Dermis

Since the major factor contributing to the aging of the facial skin is damage to and loss of the dermal collagen, an important component of any facial rejuvenation program is the stimulation of new collagen production in the dermis. Producing new collagen in the dermis of the skin has several major benefits:

New collagen in the dermis increases dermal thickness and counteracts the thinning which characterizes aging facial skin.

New collagen in the dermis has a plumping or filling effect on the age damaged areas of the dermis that have atrophied and resulted in the depressions, which underlie wrinkles. This plumping effect can reduce the depth and number of facial wrinkles.

New collagen in the dermis can more effectively provide nutritional support for the overlying epidermis and result in a healthier fresher appearing skin surface.

Step 3—Removal of Pigment and Superficial Blood Vessels

The accumulation of pigment (brown spots) and the proliferation of visible superficial blood vessels (red spots) on the surface of the skin are the skins inflammatory response to years of damaging ultraviolet sun light injury and other toxic injuries both from the environment and from within our own bodies. These changes are classic signs of facial skin aging. Removal of these blemishes imparts the following rejuvenation effects:

A homogeneous even unblemished appearance youthful skin appearance and color.

Removal of atypical damaged inflammatory lesions that may in the future evolve into more serious extensive abnormal facial lesions, such as actinic keratoses, which is a possible precursor to skin cancer.

Step 4—Relaxation of the Muscles of Facial Expression

As discussed earlier continued contraction of the muscles of facial expression throughout life results in the development of the lines of facial expression. These lines known commonly as crow's feet, frown lines, worry lines and bunny lines are noticeable facial wrinkles that impart a characteristic aged appearance to the face. Any effective facial rejuvenation program must address these significant Type 2 facial aging changes. Relaxation of the muscles of facial expression will:

Remove or soften the crow's feet, frown lines, worry lines, and bunny lines

Prevent their recurrence once facial rejuvenation has been achieved and avoid renewed Type 2 facial aging changes caused by these muscles.

Step 5—Fill Soft Tissue Defects, Deep Facial lines, and Contour Deformities

The combination of the dermal atrophy, subcutaneous fat loss, and sagging facial soft tissue structures creates several different facial deformities that are classically associated with facial aging. Inferior migration, thinning, and lengthening of the upper lip, the appearance of deep lines or depressions in the facial skin called the nasal labial fold and marionette lines, the tear trough deformity, and the "dark circle" beneath the lower eyelid are examples which impart a very aged appearance to the facial skin. Improvement in the appearance of these deformities requires volume replacement that will result in:

Softening of the appearance of these defects by plumping the depression and lessening the shadow created by the depressions.

Filling or plumping the lip to a fuller more youthful appearance.

Filling depressions caused by dermal and subcutaneous fat atrophy or the descent of soft tissues to an inferiorly placed location.

Step 6—Tighten Facial Skin

The loss of skin elasticity secondary to damage to the dermal collagen and elastin, and the atrophy of the subcutaneous fat and to a lesser extent, bony atrophy (at advanced ages) results in a downward migration or sagging of the facial skin. Clinically this results in several anatomic facial changes associated with an aged facial appearance commonly called "jowls"(loose skin folds along the jaw), turkey neck or turkey wattle (loose skin folds on the neck and beneath the chin), sagging cheek, and sagging eyebrow, which can obscure the vision if it overhangs the eye significantly. While steps 1-5 address most all of the Type 1 superficial skin aging changes, and the dynamic Type 2 facial expression induced changes, and many of the Type 2 volumetric facial aging changes, the descent of the facial skin envelope resulting from the loss of elasticity and major volumetric loss are not yet fully addressed. Tightening of the facial skin envelope is required for effective facial rejuvenation in patients who have facial skin sufficiently aged in appearance to demonstrate the anatomical changes described above in this paragraph. For these individuals tightening of the facial skin will provide:

Restoration of the cheek skin to a higher more youthful position over the cheek bone or zygomatic arch.

Restoration of the high point of the eyebrow to a position at least 1 centimeter above the supraorbital rim (the upper brow bone).

Restoration of a smooth jaw line extending from the chin to the angle of the jaw bone which lies below the ear.

Restoration of a clean neck line approximating a right angle at the intersection of a line extending from below the chin to the Thyroid cartilage (Adams apple) and from the Thyroid Cartilage down to the suprasternal notch (the top of the breast bone).

According to the present invention, the multi-step facial skin rejuvenation method of the present invention is embodied in multiple implementations, each implementation being comprised of the basic multi-step method but adapted and customized to meet the needs of the person based on age and degree of aging changes already present on the facial skin of the individual. In presently preferred embodiments of the invention the presently preferred embodiments of the method include:

Regimen A—Preventative Program;

Regimen B—Program For Early Facial Aging (Youth Maintenance);

Regimen C—For Moderate Facial Aging (Early Intervention); and,

Regimen D—For Mature Facial Aging (Advanced Therapy)

Considering each of these regimens in further detail:

Regimen A—is for an age range of 16-26 years and consists of s preventative (Prophylaxis—ForeverYoung) regimen involving two agents, one for light skin and one for dark skin.

Regimen A Includes:

Steps 1 and 2—A blend of microcrystalline beads suspended in a safe vitamin and antioxidant rich emollient will be used as a facial wash daily to cleanse and exfoliate the skin. Examples include the Preventative Exfoliation and Collagen Stimulating Formula and nutritional and vitamin support with The Forever Young Vitamin Formula and the Forever Young Age Prevention Diet as described in detail in Appendix A;

Step 3—A topical anti-oxidant cream with a sun block containing Vitamins A<C< and E—agents shown to triple the protection of sun block—will be applied daily to inhibit pigment and new blood vessel formation and prevent damage to dermal collagen, and stimulate the production of new collagen formation. Examples include the Pigment and Vessel Prevention Formula described in Appendix A;

Step 4—is unnecessary;

Step 5—Application of a Topical skin plumping cream, as described in Appendix A, where necessary; and, Step 6—The facial and total body anti-aging exercise program as described in Appendix A.

Regimen B is for an age range of (27-36 years of age and is a skin rejuvenation program for early facial aging for youth maintenance and recovery and includes two agents/formulas, one for light skin and one for dark skin:

Regimen B Includes:

Steps 1 & 2—A blend of microcrystalline beads suspended in a safe vitamin and antioxidant rich emollient fortified with a mild non prescription "fruit acid to enhance exfoliation will be used as a facial wash daily to cleanse and exfoliate the skin. Examples include Perpetual Youth Exfoliation and Collagen Production Formula, periodic mechanical exfoliation with microdermabrasion, or topical skin peels, and Forever Young Diet and Forever Young Vitamin Formula as described in Appendix A;

Step 3—A cream containing agents for pigment and new vessel control, anti-oxidants and collagen stimulating agents to replace damaged dermal collagen, such as Perpetual Youth Pigment and Vessel Control as described in Appendix A;

Step 4—Topical muscle relaxing agent to minimize lines of facial expression, as also described in Appendix A;

Step 5—Topical Skin Plumping Formula where necessary, as described in Appendix A; and, Step 6—A program of facial tightening and age reversing total body exercises as described in Appendix A.

Regimen C is for an age range of 37-45 years of age and for facial rejuvenation for moderate facial aging, also referred to as interventional therapy, and includes dark and light skin formulations. This regimen is typically used for patients between the ages of 37 and 45 when most people, especially women, begin to see visible significant signs of aging on their facial skin, although these changes have been accumulating since the mid 20"s. This is also the age range at which aggressive interventional steps must be taken if more significant facial aging changes are to be prevented.

Regimen C Includes:

Steps—1 and 2 which involve aggressive exfoliation with daily Interventional Exfoliation and Collagen Stimulating Formula as described in Appendix A and at least monthly mechanical exfoliation and stimulation with microdermabrasion, peels, and for those with significant sun damage, pigment, or acne scarring, sequential microlaser peeling at depths varying from 20 microns to 120 microns. The regimen includes a program of periodic laser and IPL therapy for stimulation of new collagen formation and involves an early intervention facial rejuvenation vitamin formula and Forever Young Diet as described in Appendix A.

Step—3 and 4—Application of a stronger pigment and vessel control cream, such as Interventional Pigment, Vessel, and Fine Line Control described in Appendix A, and a program of periodic laser and /or IPL treatments for removal of pigment and vessels, together with an with added muscle relaxing agent.

Step—4 Periodic injections of Botox injections or topical muscle relaxing agent, at intervals of 6 months to one year, for control of crows feet, frown lines, bunny lines, and worry lines;

Step—5—Application of a topical skin plumping formula together with periodic soft tissue filler injections into deep facial lines and contour deformities caused by subcutaneous fat atrophy at intervals of 6 months to one year;

Step—6 Skin tightening of brow, jaw line, and neck utilizing Radiofrequency, Infrared, and individual/or combination wavelength laser therapy such as 1064 nm, 1319 nm, and other appropriate wavelengths, or IPL broadband therapy, combined with sequential micro ablative resurfacing with erbium or CO2 lasers or other appropriate laser wavelengths when indicated; and, Continuation of anti-aging facial and body exercise program as described in appendix A.

Regimen D—is for an age range of 46 years of age up and is a facial rejuvenation program for mature facial aging and includes both dark and light skin formulations. Significant permanent severe facial aging changes begin to occur during this time period, although they are not significantly noticeable until the mid 50's for many people and people with fair skin will show changes earlier while those with dark skin will show them later. However the earlier the 6 step program is applied the better the results will be. The major event accelerating the facial aging process is the loss of hormonal support, that is, menopause for women and andropause for men, which strikingly accelerates the appearance of facial aging changes.

Regimen D Includes:

Steps—1 and 2—Aggressive exfoliation with, for example, daily applications of Advanced Exfoliation and Collagen Stimulating Formula as described in Appendix A and at least monthly mechanical exfoliation and stimulation with microdermabrasion, peels, and for those with significant sun damage, pigment, or acne scarring, sequential microlaser peeling at depths varying from 40 microns to 120 microns. Steps 1 and 2 may also include an active facial rejuvenation light therapy program utilizing laser, IPL and other light therapy together with application of Advanced Hormonal BalanceFacial Rejuvenation Vitamin Formula and Forever Young Diet with Hormonal Balance Formula as described in Appendix A;

Steps 2 and 3—A stronger pigment and vessel control cream with an added muscle relaxing agent, such as Interventional Pigment, Vessel, and Fine Line Control as described in Appendix A, and an active facial rejuvenation light therapy program utilizing laser, IPL and other light therapies;

Step—4—Periodic injections of a muscle relaxant such as Botox or topical muscle relaxing agent, at intervals of 6 months to one year, for control of crows feet, frown lines, bunny lines, and worry lines;

Step—5—Applications of Topical Skin Plumping formula such as described in Appendix A together with periodic soft tissue filler injections into deep facial lines and contour deformities caused by subcutaneous fat atrophy at intervals of 6 months to one years and injections of fat or other autologous substances for severe changes where necessary; and, Step—6—Skin tightening of brow, jaw line, and neck utilizing radiofrequency, infrared, and individual/or combination wavelength laser therapy, such as at 1064 nm, 1319 nm and other appropriate wavelengths, or IPL broadband therapy, combined with sequential micro ablative resurfacing with erbium, CO2 or other appropriate laser wavelengths when indicated, and, in individuals with advanced facial aging and lax skin, aggressive skin tightening with laser or chemical resurfacing.

Since certain changes may be made in the above described method and system, without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. A method for non-surgical rejuvenation of facial skin, comprising the steps in the order (a)-(f) as presented below:
   (a) exfoliating the facial skin,
   (b) stimulating new dermal collagen deposition,
   (c) removing at least one of pigment and superficial blood vessels,
   (d) relaxing facial expression muscles,
   (e) filling of soft tissue defects including at least one of deep facial lines and contour deformities, and
   (f) tightening of the facial skin.

2. The method of claim 1 for non-surgical rejuvenation of facial skin, further including:
   at least one of
      correcting of at least one of atrophy of subcutaneous fat and loss of bone, and
      applying at least one of a dietary regime, an exercise regime and an administering of vitamin supplements.

3. The method of claim 1 for non-surgical rejuvenation of facial skin wherein the step of exfoliating the facial skin includes:
   at least one of
      applying an emollient,
      mechanically exfoliating, and
      laser peeling.

4. The method of claim 1 for non-surgical rejuvenation of facial skin wherein the step of stimulating new dermal collagen deposition includes:
   at least one of
      applying an anti-oxident agent,
      applying collagen stimulating agent, and
      applying laser light therapy.

5. The method of claim 1 for non-surgical rejuvenation of facial skin wherein the step of removing at least one of pigment and superficial blood vessels includes:
   at least one of
      applying a pigment and vessel control agent,
      mechanically exfoliating,
      applying dermal abrasion,
      laser peeling, and
      applying light therapy.

6. The method of claim 1 for non-surgical rejuvenation of facial skin wherein the step of relaxing facial expression muscles includes:
   injecting at least one of
      a muscle paralyzing agent, and
      a muscle relation agent.

7. The method of claim 1 for non-surgical rejuvenation of facial skin wherein the step of filling of soft tissue defects includes:
   at least one of
      applying a skin plumping agent, and
      injecting a soft tissue filler.

8. The method of claim 1 for non-surgical rejuvenation of facial skin wherein the step of tightening the facial skin includes:
   at least one of
      applying radiative energy therapy, and
      applying abrasive resurfacing of the skin.

\* \* \* \* \*